United States Patent [19]

Pardekooper et al.

[11] 4,263,910
[45] Apr. 28, 1981

[54] IMPLANTATE PACKAGE, SYSTEM AND METHOD

[75] Inventors: Garrett J. Pardekooper; Kenneth E. Prince; James A. Purvis, all of Indianapolis, Ind.

[73] Assignee: Eli Lilly and Company, Indianapolis, Ind.

[21] Appl. No.: 142,411

[22] Filed: Apr. 21, 1980

Related U.S. Application Data

[63] Continuation of Ser. No. 946,109, Sep. 27, 1978, abandoned.

[51] Int. Cl.$^3$ ............................................. A61M 5/00
[52] U.S. Cl. ................................................... 128/217
[58] Field of Search ........... 128/215, 216, 217, 218 R, 128/218 N, 221, 260, 264, 272, 272, 3; 206/484.2

[56] References Cited

U.S. PATENT DOCUMENTS

| | | | |
|---|---|---|---|
| D. 242,529 | 11/1976 | Albright et al. | D9/192 |
| 1,046,962 | 12/1912 | Bullock | 200/1 R |
| 2,747,574 | 5/1956 | Lorenzo | 128/621 |
| 2,767,711 | 10/1956 | Ernst | 128/249 |
| 3,162,306 | 12/1964 | Zackheim | 206/63.2 |
| 3,474,789 | 10/1969 | Soto | 128/272 |
| 3,606,077 | 9/1971 | Faust | 226/66 |
| 3,811,564 | 5/1974 | Braber | 206/469 |
| 3,924,746 | 12/1975 | Haines | 206/530 |
| 3,993,190 | 11/1976 | Schmidgall | 206/229 |
| 4,004,565 | 1/1977 | Fischer et al. | 124/45 |
| 4,089,415 | 5/1978 | Laib | 206/484.2 |

OTHER PUBLICATIONS

Hess & Clark, Ashland, Oh. DIBESTrol-C Cattle Implants (container) and *Illustrated Directions for Use and Care of DiBESTrol-C Implanters* (outer surface of container).
Syntex Laboratories, Inc., Palo Alto, Calif., Veterinary SYNOVEX ®—S, *Steer Finishing Implants* and *Synovex Implanter* (directions for use and brochures).
Syntex Laboratories, Inc., *Synovex means real effectiveness. It takes just seconds—here are the steps* (advertisement).
Chas. Pfizer & Co., Inc., New York, N.Y., *Pfizer Stimplants for Beef Cattle and Calves* (enveloper container).
Commercial Solvents Corporation, Terre Haute, Ind., Label, *RALGRO ® Brand of Zeranol—Ball Implants for Beef Cattle* (box, label, etc.) and *Directions for Using RALGRO Ball Implants with Ball Implant Guns* and brochure, *RALGRO A Total Management Tool for Faster, More Efficient Gains in FEEDLOT STEERS & HEIFERS* (4 pages), IMC Chemical Corp., Inc., Terre Haute, Ind.

*Primary Examiner*—John D. Yasko
*Attorney, Agent, or Firm*—Jenkins, Coffey, Hyland, Badger & Conard

[57] ABSTRACT

Implantates are packaged in means capable of aseptic treatment and forming a closed cell having a portion adapted for engagement, rupture, and entry by a tool that permits removal of the implantate for use without handling of the implantate by the user. In such a package, the closed cell is formed by a film which includes portions shaped to assist rupture and entry of the cell by the tool and to assist in encompassing the implantate within the tool for its removal from the cell. The tool used in this system can be the means used to implant the implantate subcutaneously in the body of an animal. Thus, using the system of this invention, an implantate can be provided within a closed cell which is capable of aseptic treatment and transported to a remote site for use. At such a site, the closed cell can be ruptured with an implanter and the implantate can be encompassed within the implanter and removed from the cell for implantation.

13 Claims, 7 Drawing Figures

IMPLANTATE PACKAGE, SYSTEM AND METHOD

This is a continuation of application Ser. No. 946,109 filed Sept. 27, 1978, now abandoned.

This invention relates to a new package and system for use with implantates.

Implantates have been developed to introduce therapeutic agents into the body of an animal by providing uniform release of drugs over long periods of time. Such implantates comprise a drug carrier formed of an organopolysiloxane rubber composition (more generally known as silicone rubber) which is non-reactive toward the drug, non-toxic to the body, and known to be compatible with living tissue even after a prolonged implantation period. The drugs are in powder or semi-solid or liquid form, and generally have appreciable solubility in the polymer composition of the organopolysiloxane rubber composition. Such drugs are introduced from the carrier into the body of the animal by diffusion or migration interstitially between the elastomer molecules to the outer surface of the carrier from which they are removed by the animal's body fluids. The term "drug" is used in its broad sense as synonomous with therapeutic agents, medicaments, and the like, and is intended to include hormones, vitamins, antibiotics, anticoagulants, cancericidal agents, spermicidal agents, vasoactive agents, and other medicinals and medications effective to treat undesirable conditions existing in or on an animal body or in an animals's body fluids.

Such implantates are not eroded by the animal's body fluids and permit the exposure of the animal to the effect of the drug to be terminated at will by removal of the implantate. With termination of exposure of the animal to the effects of the drug thus controllable, a livestock owner has the ability to more rapidly meet the demands of the marketplace by electing to shorten the time between treatment of the animal with a drug, such as a growth stimulant, and slaughtering of the animal for use.

To provide treatment of animals, for example with estradial, and permit termination of such treatment, implantates in tubular form having lengths on the order of an inch or more and diameters of a significant fraction of an inch are used. The insertion of such implantates into the animal's body must frequently take place at a remote site, such as at a livestock ranch or at feeder lots in the field. Furthermore, the insertion of such implantates must be performed by ranch and field hands frequently under dirty conditions.

This invention permits the handling of implantates at such remote sites without their contamination. In this invention, implantates are packaged in means capable of aseptic treatment and forming a closed cell having a portion adapted for engagement, rupture and entry by a tool that permits removal of the implantate for use without handling of the implantate by the user. In such a package, the closed cell is formed by a film which includes portions shaped to assist rupture and entry of the cell by the tool and to assist in encompassing the implantate within the tool for its removal from the cell. The tool used in this system can be the means used to implant the implantate subcutaneously in the body of an animal.

A plurality of sterile implantates can be so provided for use at a remote site with such a package. In such a specific form, the package can include a relatively rigid substrate with an adhering film to form a plurality of individual cells for the implantates, arranged adjacent the edge of the substrate. The film is shaped at the end of each cell adjacent the edge of the card for engagement and rupture by an implantate removal tool. At the end remote from the edge of the substrate, the film can be shaped to accommodate a sharpened end on the implantate removal tool without rupture of the film, and the substrate can form a flap that is foldable over the remote ends of the cells to permit the package to be more easily handled and to protect the hand of the user from the sharpened end of the implantate removal tool. In one particularly desirable embodiment of the package, the film carried by the substrate is shaped to form a plurality of elongated and parallel closed cells arranged perpendicular to and adjacent to one edge of the substrate.

Thus, using the system of this invention, an implantate can be provided within a closed cell which is capable of aseptic treatment and transported to a remote site for use. At such a site, the closed cell can be ruptured with an implanter and the implantate can be encompassed within the implanter and removed from the cell for implantation. Such a system and method is capable of maintaining an implantate in a sterile condition during transportation and handling and will permit removal of the implantate for use at a remote site without contamination of the implantate through handling.

Other features and advantages of this invention will be apparent from the following specification and from the drawings in which.

Figure 5:
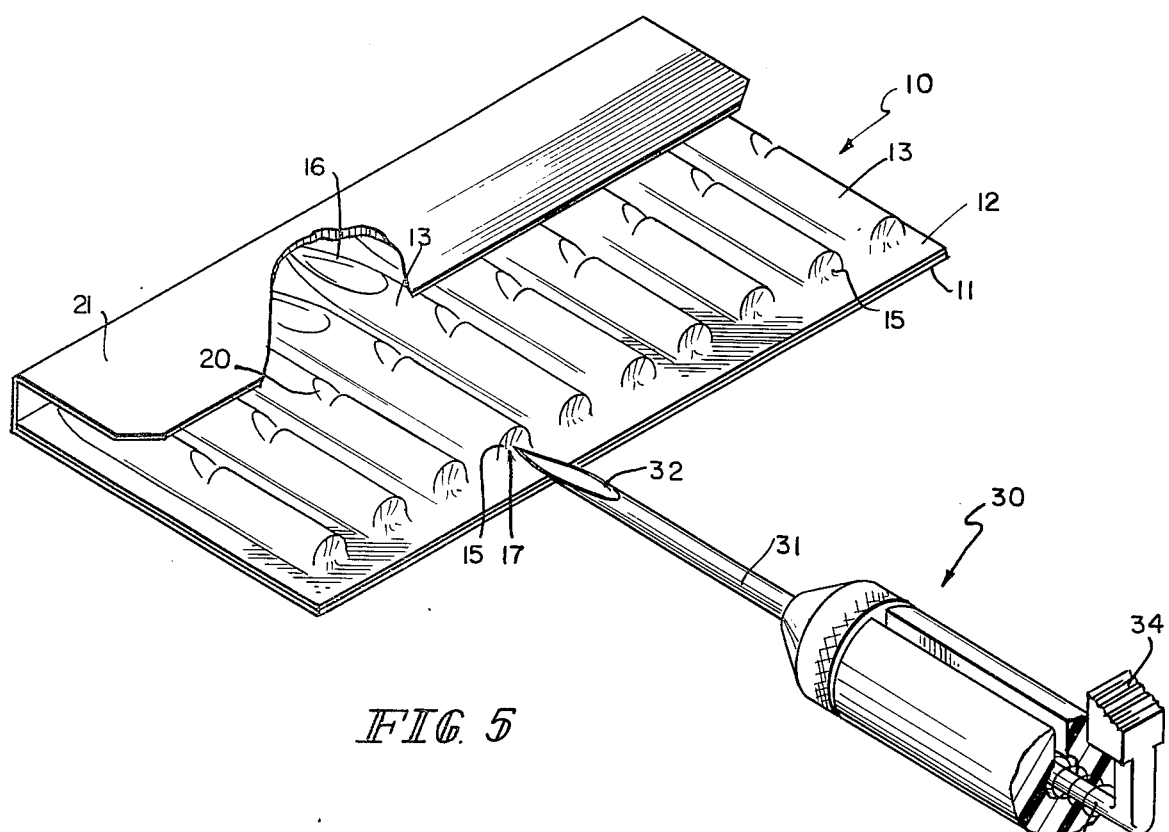
FIG. 5 is a perspective view of a system of the invention including the package of FIG. 1 and an implant removal tool positioned to enter the package for removal of an implantate within one of the cells.
Figure 6:
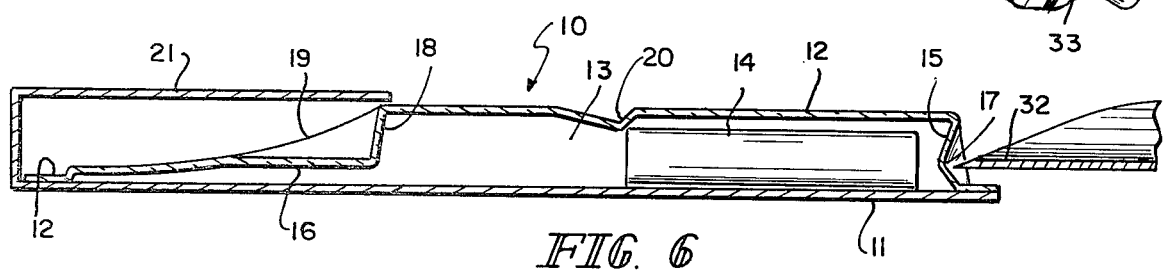
Figure 7:
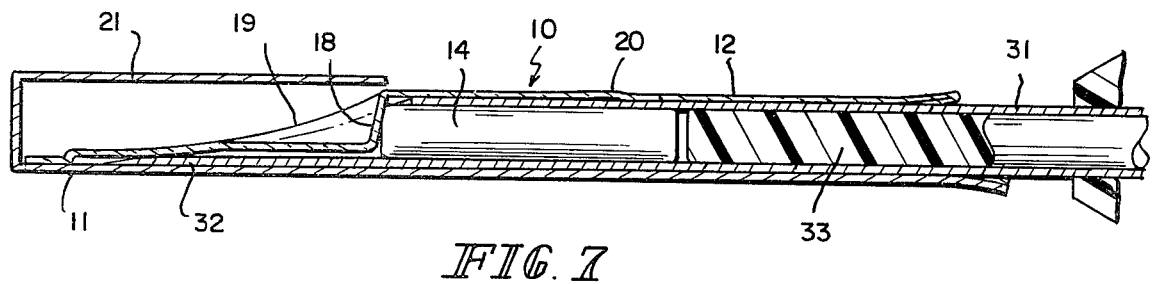

FIG. 6 is a cross-sectional view through the center of one of the closed cells of the package of FIG. 5 showing the implant removal tool engaging the end of the closed cell adjacent the edge of the package; and FIG. 7 is a cross-sectional view through the center of the cell of FIG. 6 showing the implant removal tool in cross section within the cell and encompassing the implantate for removal from the package.

The preferred embodiment of the invention illustrated herein includes a plurality of cells incorporated into a single package; however, the features of the invention are suited for use in packages containing a single cell.

Figure 1:
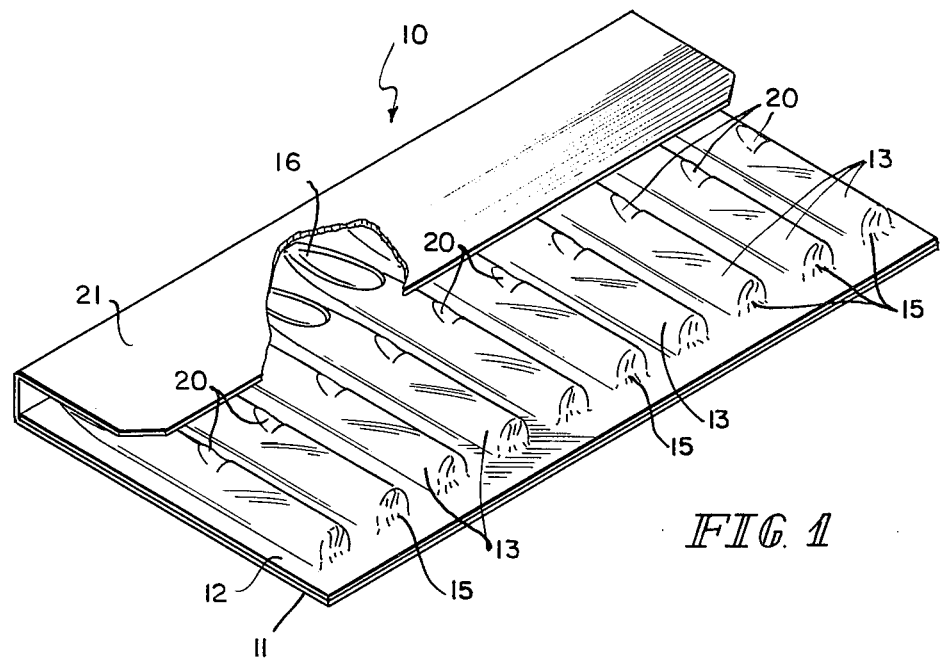
FIG. 1 is a perspective view of a package of this invention, with a portion broken away to show a complete closed cell.

FIG. 1 is a perspective view of a package 10 of this invention. Such package means forms a closed cell for an implantate, is capable of aseptic treatment, and has a portion adapted for engagement, rupture, and entry by a tool to permit removal of the implantate from the cell. The package can be formed from a relatively rigid substrate 11 such as paperboard ten to twenty thousandths of an inch thick, and a relatively rigid film 12 such as polyvinylchloride film approximately three to seven thousandths of an inch thick.

Figure 2:
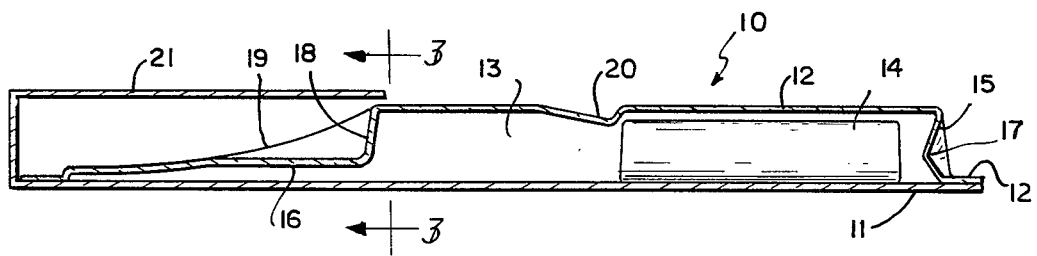
FIG. 2 is a cross-sectional view of the package of FIG. 1, taken perpendicular to a vertical plane through the center of one of the closed cells.
Figure 3:
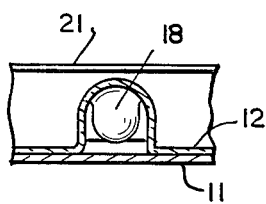
FIG. 3 is a cross-sectional view along the longitudinal axis of one of the cells taken in the direction of its end remote from the edge of the package as shown by line 3—3 of FIG. 2.
Figure 4:
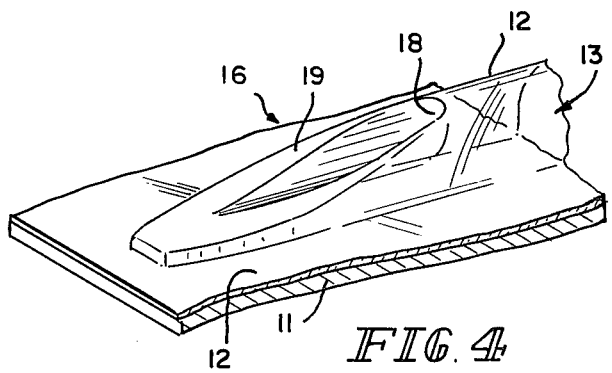
FIG. 4 is a perspective view of the end of one of the cells remote from the edge of the package.

In the embodiment shown, the film 12 forms a plurality of cells 13 arranged adjacent an edge of the substrate 11. Each of the cells 13 is elongated to contain an elongated implantate 14, as shown in FIG. 2. The film 12 thus forms a plurality of elongated closed cells 13 which are parallel and perpendicular to one edge of the rectangular substrate, with one end 15 adjacent the edge of the rectangular substrate and the other end 16 remote from the edge of the substrate. The portion of the film 12 forming the ends 15 adjacent the edge of the substrate is provided with indentations 17, as shown in FIG. 2. The indented ends 15 are thus shaped to engage the end of an implantate removal tool to assist in rupturing the film 12 at the end of the cell and in the entry of the tool into the cell. The cross section of each closed cell 13 as shown in FIG. 3 is preferably straight-sided with a semi-cylindrical upper portion. At the ends 16 of each cell 13 remote from the edge of the substrate, the film 12 is shaped to accommodate a sharpened end on the implantate removal tool without rupture of the film 12 as shown in FIGS. 1, 2, 4, and 7. The ends 16 can include depending portions 18, as shown in FIGS. 2, 3, 4, and 7 to engage an end of the implantate 14 so that the implantate 14 can be completely encompassed by the sharpened end of the implantate removal tool, and the remaining portions 19 of the ends 16 can be shaped to mate the sharpened end of an implantate removal tool. Each cell 13 may be provided with an indented wall portion 20 formed by the film 12 between the ends 15 and 16 of cells to prevent buckling of the flexible elongated implantate 14 and to assist the implantate 14 within the encompassing tool.

The rectangular substrate 11 can form a flap 21 that can be folded over the ends 16 of the cells to permit the package to be more easily grasped and to provide an additional measure of protection for the hand of the user in the event the sharpened end of the implant removal tool may accidentally rupture the film 12 adjacent end 16.

Packages of this invention can be of any size, but one particularly convenient size is formed with a rectangular card approximately six and one-half inches wide and four and three-quarters inches long. Ten closed cells can be formed like blisters on the card by a transparent polyvinylchloride film attached to and carried by the card. Each cell formed by the plastic film is approximately two and three-quarters inches in length with a cross-sectional area approximately one-quarter of an inch high and one-quarter of an inch wide to accommodate elongated flexible tubular implantates about one and one-quarter inches long and about three-sixteenths of an inch in diameter.

In the manufacture of such packages, a polyvinylchloride film is molded into the cell configuration that is wanted, and in this molding step some control of wall thickness can be obtained to provide more rigidity to the side walls of the cells, reduced thickness at the ends of the cells to be opened and greater thickness at the ends of the cells that are exposed to a sharpened end of the removal tool. A cardboard substrate having a heat-sealable adhesive coating is used, and the film is preferably attached to the substrate by adhesion of planar portions of the film adjacent the cells with this coating.

The system of this invention includes a second means 30 in the form of a tool to engage and rupture the package and to encompass and carry the implantate from within the package. Such a tool for removal of the implantate can be the means used to implant the implantate and can have a sharpened tubular member 31 having a straight bore and an end 32 sharpened at an acute angle.

As shown in FIG. 5, the implanter includes an ejector 33 operable by a tab 34 to eject the implantate 14 from within the tubular member 31, for example, after the sharpened end 32 has pierced the skin of an animal for location of the implantate 14 under the skin of the animal. The sharpened end 32 will engage the indentation 17 at the end 15 of closed cell 13 adjacent the edge of the substrate 11 as shown in FIG. 5 and FIG. 6. The indented end 15 locates the tool end and assists in the rupture of the film 12 by the sharpened end 32 of the removal tool. After the film 12 is ruptured by the end 32 of the tool, the tubular member 31 enters and slides within the cell 13. As shown in FIG. 7, implantate 14 is engaged by portion 18 of the film 12 at the end 16 of the cell remote from the edge of the card. The remainder 19 of the end 16 of the cell remote from the edge of the card accommodates and mates the sharpened end 32 of tool 30, as shown in FIGS. 6 and 7, and as shown in FIG. 7, portion 18 permits implantate 14 to be completely encompassed by tubular member 31 within the cell 13 so that it may be carried and removed from the cell by the tubular member. The indented wall means 20 assists the user in locating a flexible implantate 14 within the opening of the sharpened end 32 of the tubular member 31 by preventing its buckling within the cell, and the removal of the implantates from the package is further assisted by use of a film 12 that is transparent.

An example of a method of use of the system and package of this invention can include the use of an implantate about one and one-quarter inches long and three-sixteenths of an inch in diameter comprising an organopolysiloxane composition containing a growth stimulant such as twenty-four milligrams of estradial. Such an implantate can be provided within a closed cell formed from a polyvinylchloride film of a few mils thickness capable of sterile handling. The implantate thus enclosed may be handled and transported without contamination to a rural feeder lot for use. An implanter having a sharpened tubular member about one-quarter inch in diameter can be used to rupture the closed cell and to encompass the implantate while it is within the cell for removal of the implantate from the cell. Upon removal of the implantate from the cell, the implanter may be used to pierce the skin of a steer's ear and to eject the implantate subcutaneously within the ear of the steer. In this method, where a plurality of sterile implantates are to be used, they may be provided at such a remote site within a plurality of contiguous closed cells which have been treated to maintain a sterile condition. A user can, by grasping the plurality of contiguous closed cells in one hand and the implanter in the other hand, engage the indented end of a cell with the sharpened tubular end of the implanter, rupture the end of the cell and encompass the implantate within the cell for removal and implantation.

Thus, the package, system, and method are adapted to permit the sterile handling of an implantate by the use of first means forming a closed cell for the implantate, being capable of aseptic treatment, and having a portion adapted for engagement, rupture, and entry by a second means adapted to engage the said portion of the first means and to rupture and enter the closed cell and encompass the implantate within the cell for removal and use. This system permits the subcutaneous implantation of implants without exposure of the implant to contamination in handling and transportation at a remote site of use.

The specific embodiment of the invention shown and described above is capable of modification without departure from the scope of the following claims.

We claim:

1. A system adapted to permit the sterile subcutaneous implantation of a solid implant comprising
    an implant package carrying a solid subcutaneous implant and formed from a relatively rigid transparent film capable of aseptic treatment and including a first portion adapted for engagement, rupture and entry by an implanter and a second portion to engage and position the solid implant for insertion into the implanter, and
    an implanter adapted to engage and rupture said first portion of the film and to enter said implant package and encompass the solid implant within the package and to remove and carry the implant for ejection subcutaneously.

2. A system for the sterile provision of an elongated subcutaneous implantate to an implanter comprising
    first means forming a sterile cell for the elongated implantate including a relatively rigid film capable of aseptic treatment, and
    second means forming an implanter and including a sharpened tubular member having a straight bore and being adapted to encompass the elongated implantate, and an ejector to eject an implantate carried within the bore of the tubular member,
    said first means forming a sterile cell having one indented outer end adapted for engagement, rupture and entry by the sharpened tubular member of the second means and the other end adapted to prevent movement of the implantate and to assist in urging the implantate within the tubular member, said first means permitting the removal of the implantate by the second means while maintaining its sterile condition.

3. A system adapted to permit the handling of an implantate without contamination comprising
    first means forming a relatively rigid closed cell for an implantate, being capable of aseptic treatment and having an indented outer portion adapted for engagement, rupture and entry by an implantate carrier, and
    second means including an implantate carrier adapted to engage said indented portion of the first means and to rupture and enter the closed cell and encompass the implantate within the cell for removal and use.

4. The system of claim 3 wherein said first means forms an elongated cell from a relatively rigid transparent plastic film, said second means includes a tubular member with a straight bore and a sharpened end, and the indented portion of the first means adapted for engagement, rupture and entry by an implantate carrier is an indented end of the film forming the cell to position the sharpened end of the second means so that the sharpened end pierces the plastic film, said first means permitting the tubular carrier to slide easily within the elongated cell and urging the implantate to enter within and be carried by the tubular member.

5. The system of claim 4 wherein the first means is shaped at the end of the cell remote from the indented end to mate the sharpened end of the tubular member without rupture of the plastic film and to urge the implantate substantially entirely within the tubular carrier.

6. The system of claim 3 wherein said first means includes a relatively rigid substrate and a film that is attached to said substrate and, with said substrate, forms a plurality of blister-like cells arranged in an array adjacent an edge of the substrate, said portion adapted for engagement, rupture and entry includes portions of the film forming the cells and close to the edge of the substrate.

7. The system of claim 6 wherein said second means includes a tubular member with a straight bore and sharpened end, said relatively rigid substrate is a rectangular paperboard card of such size that it is easily grasped by hand, said plurality of cells formed by said film are elongated and arranged in a parallel array with one end of each cell located closely adjacent one edge of the card, said film forms indentations at said ends of the cells to engage the sharpened end of the tubular member of the second means and assist rupture of the ends and entry of the tubular member within the cells and, further, said film, at the end of the cells remote from the edge of card, is shaped to accommodate the sharpened end of the tubular member without rupture of the film, and the rectangular paperboard forms a flap that is foldable at the remote ends of the cells to permit the first means to be more easily grasped by hand and to protect the hand of the user.

8. A method permitting subcutaneous implantation without exposure of a solid implant to contamination, comprising
    providing a solid implant within a closed cell formed from a film capable of aseptic treatment to permit the handling and transport of the implant without contamination,
    rupturing the closed cell with an implanter at the site of use, encompassing the solid implant within the implanter while it is within the cell and removing the implant from the cell for use.

9. A method of providing sterile implantation of a plurality of subcutaneous implantates at a remote site comprising
    providing aseptically a plurality of sterile implantates within a plurality of contiguous closed cells formed from material capable of maintaining their sterile condition,
    transporting the plurality of sterile implantates to a remote site of use within the plurality of contiguous closed cells,
    grasping the plurality of contiguous closed cells in one hand and an implanter having a sharpened tubular end in the other hand, and piercing the material from which the cells are formed, encompassing an implantate in one of the cells within the tubular end of the implanter and removing the implantate from the cell for implantation.

10. A system adapted to permit the handling of an implantate without contamination comprising first means including a relatively rigid substrate and a film that is attached to said substrate forming a plurality of blister-like cells that contain a plurality of elongated implantates and are adapted for engagement, rupture and entry by an implantate carrier; and second means, including a tubular member with a straight bore and a sharpened end, adapted to engage and to rupture and enter the blister-like cells and to encompass the implantates within the cells for their removal and use, said relatively rigid substrate being a rectangular paperboard card of such size that it is easily grasped by hand, said plurality of blister-like cells being elongated and arranged in a parallel array with one end of each cell located adjacent one edge of the card, the ends of the cells adjacent the one edge of the card-forming indentations to engage the sharpened end of the tubular member of the second means and to assist rupture of said ends and entry of the tubular member within the cells and the other ends of the cells being shaped to accommodate the sharpened end of the tubular member without rupture of the film, the rectangular paperboard forming a flap that is foldable at the other ends of the cells to permit the first means to be more easily grasped by hand and to protect the hand of the user.

11. A system adapted to permit the sterile subcutaneous implantation of an implant comprising
  an implant package forming a sterile cell for a solid elongated implant from a relatively rigid material capable of aseptic treatment and including an end portion being shaped to engage the end of an implanter so that the end of the cell is easily ruptured by the implanter, the package being shaped to permit insertion of the implanter into the cell and with the other end of the cell shaped to urge the solid elongated implant into the implanter without further rupture of the package and further including a relatively rigid portion adjacent the other end of the cell to permit the package to be more easily grasped by hand as to protect the hand of the user, and
  an implanter adapted to engage and rupture the end of said package and to enter said implant package and encompass the solid elongated implant within the package and to remove and carry the implant for ejection subcutaneously.

12. A system for sterile provision of a subcutaneous implantate to an implanter comprising
  first means forming a plurality of sterile cells for elongated implantates from a relatively rigid film capable of aseptic treatment, said film being adhered to a relatively rigid card with the plurality of cells being arranged so that each cell has one end adjacent an edge of the card, said film at the end of each cell adjacent the edge of the card being adapted for engagement, rupture and entry by an implanter, and
  second means forming an implanter and including a sharpened tubular member having a straight bore and being adapted to encompass an implantate within the cells of the first means and an ejector to eject the implantate carried within the bore of the tubular member, said first means permitting the removal of the implantate by the second means while maintaining its sterile condition.

13. A system adapted to permit the handling of an implantate without contamination comprising
  first means including a relatively rigid substrate and film that forms a plurality of blister-like cells that contain a plurality of elongated implantates and are adapted for engagement, rupture and entry by an implantate carrier; and
  second means, including a tubular member with a straight bore and a sharpened end, adapted to engage and to rupture and enter the blister-like cells and to encompass the implantates within the cells for removal and use,
  said first means being of such size that it is easily grasped by hand, said plurality of blister-like cells being arranged with one end of each cell located adjacent one edge of the first means, the ends of the cells adjacent the one edge of the first means being adapted to engage the sharpened end of the tubular member of the second means and to assist rupture of said ends and entry to the tubular member within the cells, and the other ends of the cells being shaped to accommodate the sharpened end of the tubular member without rupture of the film, said first means forming a portion adjacent the other ends of the cells to permit the first means to be more easily grasped by hand and to protect the hand of the user.

* * * * *

UNITED STATES PATENT AND TRADEMARK OFFICE
CERTIFICATE OF CORRECTION

PATENT NO. : 4,263,910
DATED : April 28, 1981
INVENTOR(S) : Garrett J. Pardekooper; Kenneth E. Prince; and James E. Purvis It is certified that error appears in the above-identified patent and that said Letters Patent are hereby corrected as shown below:

Claim 13, line 20, delete "to" and insert therefor --of--.

Signed and Sealed this

First Day of September 1981

[SEAL]

Attest:

GERALD J. MOSSINGHOFF

Attesting Officer

Commissioner of Patents and Trademarks